US005863297A

United States Patent [19]

Walter et al.

[11] Patent Number: 5,863,297

[45] Date of Patent: Jan. 26, 1999

[54] MOLDABLE, HAND-SHAPABLE BIODEGRADABLE IMPLANT MATERIAL

[75] Inventors: Mary Ann Walter; Neil C. Leatherbury; Mark Q. Niederauer, all of San Antonio, Tex.

[73] Assignee: OsteoBiologics, Inc., San Antonio, Tex.

[21] Appl. No.: 727,204

[22] Filed: Oct. 8, 1996

Related U.S. Application Data

[63] Continuation-in-part of Ser. No. 540,788, Oct. 11, 1995, Pat. No. 5,716,413.

[51] Int. Cl.[6] .......... A61F 2/28

[52] U.S. Cl. .......... 623/16; 623/11; 623/66; 623/901; 264/41; 264/219; 264/232; 264/349

[58] Field of Search .......... 623/1, 2, 11, 12, 623/16, 18, 66, 901; 606/151, 152, 153, 154, 155; 600/29, 30, 32; 264/41, 219, 232, 349; 128/898

[56] References Cited

U.S. PATENT DOCUMENTS

| | | | |
|---|---|---|---|
| 3,919,773 | 11/1975 | Freeman | 32/10 A |
| 3,972,961 | 8/1976 | Hammer et al. | 525/183 |
| 4,535,485 | 8/1985 | Ashman et al. | 623/16 |
| 4,547,390 | 10/1985 | Ashman et al. | 427/2 |
| 4,655,980 | 4/1987 | Chu | 264/102 |
| 4,722,948 | 2/1988 | Sanderson | 523/115 |
| 4,744,365 | 5/1988 | Kaplan et al. | 128/335.5 |
| 4,786,446 | 11/1988 | Hammar et al. | 264/232 |
| 4,839,130 | 6/1989 | Kaplan et al. | 264/235 |
| 4,844,854 | 7/1989 | Kaplan et al. | 264/235 |
| 4,909,979 | 3/1990 | Possis et al. | 264/232 |
| 4,963,489 | 10/1990 | Naughton et al. | 435/240.1 |
| 5,032,508 | 7/1991 | Naughton et al. | 435/32 |
| 5,041,138 | 8/1991 | Vacanti et al. | 623/16 |
| 5,057,261 | 10/1991 | Ohori et al. | 264/232 |
| 5,124,103 | 6/1992 | Kaplan et al. | 264/102 |
| 5,160,490 | 11/1992 | Naughton et al. | 435/285 |
| 5,290,494 | 3/1994 | Coombes et al. | 264/41 |
| 5,492,697 | 2/1996 | Boyan et al. | 623/11 |
| 5,527,341 | 6/1996 | Gogolewski et al. | 606/232 |
| 5,569,250 | 10/1996 | Sarver et al. | 606/69 |
| 5,582,670 | 12/1996 | Andersen et al. | 156/242 |
| 5,607,474 | 3/1997 | Athanasiou et al. | 623/66 |

FOREIGN PATENT DOCUMENTS

| | | | |
|---|---|---|---|
| WO 9215340 | 9/1992 | WIPO . | |
| WO 9222336 | 12/1992 | WIPO . | |
| WO 9315694 | 8/1993 | WIPO . | |
| WO A 95 03011 | 2/1995 | WIPO | A61F 2/28 |
| WO A 95 22360 | 8/1995 | WIPO | A61L 27/00 |

OTHER PUBLICATIONS

Brekke, J.H. (1995), "A Rationale for Delivery of Osteoconductive Proteins," *Tissue Engineering* 2:97–114.

Brittberg, M., et al., "Treatment of Deep cartilage Defects in the Knee with Autologous Chondrocyte Transplantation," *New Engl. J. Med.* (1994) 331:889–895.

Brown, T.D. and Singerman, R.J., "Experimental Determination of the Linear Biphasic Constitutive Coefficients of Human Fetal Proximal Femoral Chondroepiphysys" (1986), *J. Biomech.* 19(8):597–605.

Frank Linde, "Elastic and viscoelastic properties of trabecular bone by a compression testing approach," (Apr., 1994) *Danish Med. Bull.* vol. 4, No. 2.

*International Search Report*, PCT/US96/16049 dated Feb. 14, 1997.

Product brochure for "*LactoSorb®" Resorbable Craniomaxillofacial Fixation* of W. Lorenz Surgical, Inc., Jacksonville, FL 32218.

*Primary Examiner*—Mickey Yu
*Assistant Examiner*—Francis K. Cuddihy
*Attorney, Agent, or Firm*—Greenlee, Winner and Sullivan, P.C.

[57] ABSTRACT

This invention provides molded, biodegradable porous polymeric implant materials having a pore size distribution throughout the material which is substantially uniform. These materials can be molded into implants of any desired size and shape without loss of uniformity of pore size distribution. The implants are useful as biodegradable scaffolds for cell growth in healing of tissue defects. When manufactured to have an aspect ratio greater than about 3, the implants can be further hand-shaped to fit the defect into which they are placed and the desired shape for the regrown tissue.

23 Claims, No Drawings

MOLDABLE, HAND-SHAPABLE BIODEGRADABLE IMPLANT MATERIAL

CROSS-REFERENCE TO RELATED APPLICATIONS

This application is a continuation-in-part of U.S. Ser. No. 08/540,788 filed Oct. 11, 1995, now U.S. Pat. No. 5,716,413, issued Feb. 10, 1998 fully incorporated herein by reference.

FIELD OF THE INVENTION

This invention is in the field of biodegradable polymeric implant materials, specifically such materials which are moldable into a wide variety of sizes and shapes and which can be hand-shaped at body temperature, while maintaining structural integrity.

BACKGROUND OF THE INVENTION

Biodegradable polymers useful for implantation into tissue defects and providing scaffolding for tissue ingrowth have been described, for example, in PCT publication WO 9315694, incorporated herein by reference. Such polymers may be manufactured to have mechanical properties matching those of the tissue into which they are to be implanted.

Implants formed of biodegradable polymeric materials may be preseeded with cells of the desired tissue type, for example as described in U.S. Pat. Nos. 4,963,489, 5,032,508, 5,160,490 and 5,041,138.

Implant materials as described above generally contain pores and/or channels into which the tissue grows as the biodegradable material erodes, thus providing new tissue growth of roughly the same size and shape as the implant.

A shapable implant material useful for a dental implant is described in U.S. Pat. No. 3,919,773 to Freeman (Sybron Corp.) issued Nov. 18, 1975 for "Direct Moldable Implant Material," however this implant material is not biodegradable.

PCT publication WO 92/15340 dated 17 Sep., 1992 of Lundgren et al. (Guidor AB) discloses a malleable bioresorbable material used to repair periodontal defects around the tooth. Polylactic acid (PLA) and copolymers of polylactic acid and polyglycolic acid (PGA) are disclosed as usually being very brittle in their pure state. The reference discloses modifying the polymers with plasticizing agents to make them more malleable. The plasticizing agents tend to cause undesirable swelling of the polymers in vivo and to decrease structural stability; however, through careful selection of the plasticizer and polymer and through the use of 10 $\mu$m perforations through the material, swelling can be minimized. Such perforations can be created by a laser process as described in PCT Publication WO 92/22336 dated 23 Dec., 1992 to Mathiesen, et al. (Guidor, AB).

U.S. Pat. Nos. 4,844,854 issued Jul. 4, 1989 for "Process for Making a Surgical Device Using Two-phase Compositions," 4,744,365 issued May 17, 1988 and 5,124,103 issued Jun. 23, 1992 for "Two-Phase Compositions for Absorbable Surgical Devices," and 4,839,130 issued Jun. 13, 1989 for "Process of Making an Absorbable Surgical Device," to Kaplan et al. (United States Surgical Corporation) disclose that biodegradable surgical devices of PLA/PGA can be made less brittle by using a two-phase polymer having a continuous lactide-rich phase interpolymerized with a continuous glycolide-rich phase or a continuous lactide-rich phase having dispersed throughout it discrete particles of a glycolide-rich phase. The material is then annealed to raise the temperature at which the material can be distorted. Malleability is thus disclosed as an undesirable property.

As discussed above, it is desirable that a biodegradable implant designed for tissue ingrowth have mechanical properties similar to those of the tissue into which it is placed. Typically accepted values for the elasticity (Young's modulus) of cartilage are less than 1 MPa (Brown and Singerman (1986), J.Biomech. 19(8):597–605). Poisson's ratio (measuring the tendency of the material to distort sideways when pressed upon from the top) values for cartilage are low, no more than about 0.3 (Frank Linde (April, 1994) Danish Med. Bull. Volume 4, No. 2).

It is thus apparent that providing a biodegradable polymeric material with a low Poisson's ratio, which is also hand-shapable at body temperature for use as an implant for promotion of cartilage, bone and other tissue ingrowth is not a trivial problem. A simple malleable substance having a high Poisson's ratio would not be suitable.

Porous biodegradable polymeric implant materials for use as scaffolds for cell ingrowth have previously been limited by the difficulty in achieving uniform porosity in implants of a size larger than a few millimeters in any dimension. Molding such materials in closed molds in vacuum ovens has resulted in the formation of scattered large bubbles and thin spots. Cell ingrowth is best encouraged in a material of uniform porosity. Thus, there is a need for a method of making a biodegradable implant material larger than a few millimeters in cross section with pores of uniform size and distribution.

In traditional bone graft procedures, autogenous cancellous bone from a source such as the iliac crest is often used for filling bone defects. Allogenic bank bone has been advocated as an alternative to autogenous bone, but the effectiveness of the graft is often compromised by nonunions, fatigue fractures, and both clinical and histological evidence of resorption of the graft. Further, allogenic bank bone is often in short supply and may carry disease factors. A major disadvantage in using autogenous bone from the patient's iliac crest is that taking this material is an extremely painful procedure (patients undergoing spine fusions tend to complain more about iliac crest pain than spine pain). Sterile materials useful as substitutes for autogenous and allogenic bone are therefore desirable, especially sterile biodegradable materials serving as scaffolds for in-growing bone.

Biodegradable implant materials for use in healing bone defects include particulate materials such as those described in Ashman, et al. U.S. Pat. Nos. 4,535,485 issued Aug. 20, 1985 for "Polymeric Acrylic Prosthesis" and 4,547,390 for "Process of Making Implantable Prosthesis Material of Modified Polymeric Acrylic (PMMA) Beads Coated with PHEMA and Barium Sulfate." These materials bond together inside the defect to form a porous mass. This implant material is not disclosed to have the mechanical properties of bone. It is desirable in promoting tissue ingrowth to provide an implant material with properties similar to those of the tissue in question insofar as possible to provide a microenvironment such that cells growing into the implant will find conditions as close as possible to the natural conditions for which they were designed. This invention provides such particulate materials.

SUMMARY OF THE INVENTION

One aspect of this invention provides a molded, biodegradable, porous polymeric implant material having at room temperature (20° to 25° C.), a Poisson's ratio less than about 0.3, preferably less than about 0.25, and more preferably less than about 0.1, and a porosity between about 60 volume percent and about 90 volume percent, preferably between about 60 and about 80 volume percent, and more preferably between about 65 and about 75 volume percent, wherein the pore size distribution throughout the material is substantially uniform, and having an aspect ratio of about 3 or more, wherein said molded implant material is hand-shapable at or slightly above body temperature without loss of structural integrity. It is critical that the porosity not be greater than about 90%. Implants with too great a porosity cannot provide the stiffness required to promote cell differentiation which requires a stiffness comparable to the tissue type, e.g., cartilage or bone, ingrowing into the implant.

The term "substantially uniform" in reference to pore size distribution throughout the material means that the size distribution of pores as measured in every portion of the material is the same. In the preferred embodiment, target or average pore size is about 100 μm to 200 μm diameter, and this average pore size is found in all portions of the material. A range of pore sizes is present above and below this average, e.g., about 5 μm to about 400 μm, and this range is substantially the same in all portions of the material. The pores are substantially evenly distributed throughout the implant material so that the density of the material at different points does not vary.

The term "aspect ratio" as used herein refers to the ratio of the longest dimension of the implant to the shortest dimension of the implant. For example, a molded wafer of this invention having the dimensions 20×40×3mm would have an aspect ratio of 40/3, or 13.3.

The term "structural integrity" as used herein means that the porosity and distribution of the pores does not significantly change, and the material does not crack or break when it is hand-shaped as described herein. As the implant materials of this invention are biodegradable, they maintain structural integrity for a period of time sufficient to effect tissue ingrowth and healing of the defect into which they are placed and subsequently biodegrade.

The term "hand-shapable" as used herein means that the material may be distorted by hand or by hand tools, so as to be shaped to fit a defect, or twisted and bent to provide desired support for tissue regrowth. The term does not refer to shaping by means of cutting tools.

The hand-shapability of the implant material is correlated with its mechanical properties, e.g. elasticity (also referred to as "stiffness" herein) and compressibility. Young's modulus defines the elasticity of a material, measured as the stress divided by the strain. Young's modulus is a measure of how much force must be applied to the material per unit area to deform it a given amount per unit length. Poisson's ratio is a measure of how much the material will contract in the directions at right angles (sideways) to the direction of stretching (as when a rubber band becomes thinner when stretched), or how much it will expand sideways when compressed (as when a ball of clay expands sideways when compressed from the top).

At body temperatures, and slightly above, the elasticity of the materials of this invention increases (Young's modulus decreases) so that the materials are generally more easily hand-shaped than at room temperature. The materials of this invention may be hand-shaped at body temperatures; however, it is preferred they be warmed to at least about 45° C. and more preferably to at least about 50° C., such as by warming on a hot plate prior to shaping. They should not be warmed about a temperature so high that they are uncomfortable to the touch.

Polymeric implant materials of this invention can be molded during manufacture into a wide variety of shapes and sizes to address many different tissue defect situations. The molded materials can be further hand-shaped by bending or can be carved to suit each individual implant application.

It is desirable in the implant materials of this invention to have structural properties, including mechanical properties such as elasticity, similar to those of the tissue into which the implant is to be placed. It is desirable that the implant materials be porous to facilitate tissue ingrowth. In general, the implant materials of this invention preferably have a Young's modulus between about 0.1 and about 200 MPa at room temperature, more preferably between about 0.1 and about 50 Mpa, and most preferably between about 0.1 and about 5 MPa or 10 MPa. Cartilage has a Young's modulus of less than about 1.0 MPa, and thus implant materials of this invention designed to be placed next to cartilage tissue preferably have a Young's modulus less than about 1.0 MPa. Bone has a Young's modulus from about 1.0 up to about 1700 MPa. However, for hand-shapability the Young's modulus at shaping temperature should not be greater than about 10 MPa. A preferred embodiment has a glass transition temperature (Tg) between about 38 and about 50.

This invention also provides molded, porous, biodegradable implant materials having a porosity between about 60 and 90 volume percent wherein the pore size distribution throughout the material is substantially uniform, and wherein said molded materials have at least one dimension greater than about 7 mm. Prior attempts to make such implants have failed because of the inability of prior workers to achieve uniform porosity when the dimensions of the implant exceeded 7 mm.

These implant materials having uniform porosity may have Young's moduli at room temperature up to or greater than that of bone, i.e. up to about 1700 MPa or greater. Preferably they have elasticities, Poisson's ratios and porosities as described above.

The implant materials may be used to make multi-phase implants such as the two-phase implants as described in PCT publication WO 9315694, incorporated herein by reference. These two-phase implants preferably have an upper cartilage phase and a lower bone phase and are inserted into a defect extending from cartilage into bone with the appropriate phases adjacent the same tissues.

The term "cartilage phase" as used herein means that the material has mechanical properties, e.g. stiffness or elasticity, substantially the same as cartilage. Similarly the term "bone phase" means that the material has mechanical properties substantially the same as bone. In a preferred embodiment of the two-phase implant, each phase has a different color to aid in distinguishing the phases so as to correctly place each phase adjacent the appropriate tissue.

The implant materials of this invention preferably have an average pore size of between about 5 μm and about 400 μm, more preferably between about 100 μm and about 200 μm.

It is preferred that the pores be interconnected to allow free flow of fluid therethrough. It is also preferred for cartilage phase implants that the implant not contain large channels having a diameter greater than about 1 mm, as this may make it difficult for ingrowing cells to bridge the gap without formation of fibrous tissue. Larger channels may be present in bone phase implants, as these can be packed with blood and marrow cells, when the implant is placed in vivo to encourage rapid cell growth. High porosities are preferred in the implants of this invention, consistent with maintaining structural integrity, as these provide most useful scaffolds for tissue ingrowth. The polymeric implant materials of this invention may also comprise cells compatible with the host for which they are intended, for example as described in the above-referenced patents directed to polymeric scaffold materials seeded with cells. Implant materials of this invention, with and without channels, may be infiltrated with nutrient and/or cellular material such as blood and narrow cells, cartilage cells, perichondrial cells, periosteal cells, and other cells of mesenchymal origin, e.g., osteoblasts, chondrocytes, and their progenitors, adipocytes, muscle cells, tendon cells, ligament cells, dermal cells and fibroblasts, to facilitate tissue growth.

A number of suitable biodegradable polymers for use in making the materials of this invention are known to the art, including polyanhydrides and aliphatic polyesters, preferably polylactic acid (PLA), polyglycolic acid (PGA) and mixtures and copolymers thereof, more preferably 50:50 to 80:20 copolymers of PLA/PGA, most preferably 70:30 to 80:20 PLA/PGA copolymers. Single enantiomers of PLA may also be used, preferably L-PLA, either alone or in combination with PGA. Polycarbonates, polyfumarates, caprolactones, trimethylene carbonate, polydioxanone and polyhydroxybutyrate may also be used to make the implants of this invention. The polymer preferably has an average molecular weight between about 30,000 daltons and about 150,000 daltons prior to use, more preferably between about 60,000 daltons and about 120,000 daltons.

The polymers are designed to biodegrade in vivo over a period of weeks. Preferably the materials maintain their structural integrity so as to serve as supportive scaffolds for ingrowing tissue for a period of at least about two weeks, and preferably about four to ten weeks for cartilage repair, and thereafter biodegrade. For bone repair, the materials maintain their structural integrity for at least about two weeks and preferably about three to eight weeks, and thereafter degrade.

The implant materials of this invention may be formed into convenient sizes and shapes during manufacturing, such as wafers, tubes, cubes, balls, cylinders and the like up to about 100 mm thick, including irregular shapes. For hand-shapable use, preferred forms are wafers having an aspect ratio greater than about 3. The die-punched wafers produce cylinders, chunklets and resultant honeycomb lattices as hereinafter described. The implant materials may be reduced in size to particles of preferably about 50 μm to about 1 cm in diameter, e.g., by shredding as hereinafter described. The implant materials tend to retain their shape at room temperature for ease in shipping and storing. However, in one embodiment of this invention, when warmed, e.g., in the physician's hands or by heating means such as a hot plate, to about 45° C. to about 50° C., and preferably not above a comfortable handling temperature, e.g., about 50° C., and/or placed within a tissue defect in a patient's body, they may be readily hand-shaped to conform to the shape of the defect and the desired shape for the regrown tissue. The implant materials of this invention may be shaped to (1) repair facial bone defects and certain defects in the mandible and maxilla; (2) dental defects such as alveolar ridge defects; and (3) other bone defects such as defects in the spine, cranium, tibia, radius, glenoid fossa, etc. New bone growth, taking the shape of the implant, can thus be directed to match the existing defect structures. The materials of this invention can also be used in other bone repairs such as spinal fusions, or used in cartilage repair such as resurfacing, e.g. femoral condyle resurfacing, or repair of cartilaginous tissue such as in the nose and ears, ribs, and chin.

The implant materials of this invention are also readily carvable, and excess material can be cut from the implant in the process of sizing and shaping the material to fit the defect.

After hand-shaping to fit the defect, the implant material may be sutured, glued or otherwise secured into place if desired. Techniques for suturing cartilage are known to the art, e.g. as described in Brittberg, M., et al. (1994), "Treatment of Deep cartilage Defects in the Knee with Autologous Chondrocyte Transplantation," New Engl. J. Med. 331:889–895. Glues known to the art such as fibrin glue, cyanoacrylate, or others, may be used to secure the implant in place. Other securing means are known to the art including bioresorbable screws, staples or other fixation devices. At body temperature, the tendency of the implant to return to its pre-shaped form is reduced from this tendency at room temperature, and suturing to maintain the desired shape of the implant may not be necessary since the implant may be held in place with surrounding soft tissue.

The implant materials of this invention may also incorporate bioactive agents such as enzymes, growth factors, degradation agents, antibiotics and the like, designed for release over time, as described in U.S. patent application Ser. No. 08/196,970 incorporated herein by reference.

For best biocompatibility it is preferred that the implant material be substantially free of solvent. It is recognized that some residual solvent will be left in the polymer, but preferably less than about 100 ppm. Solvents known to the art may be used, e.g., acetone, methylene chloride or chloroform.

The materials of this invention are readily sterilizable, have been found safe and effective in pre-clinical animal studies, and are safe for use in the human body.

This invention also comprises a method for making a molded biodegradable, porous polymeric implant material of a desired geometry, including a material as described above, wherein the pore size distribution throughout the material is substantially uniform, comprising:

a) preparing a precipitated gel-like polymer mass;
b) extracting liquid from the polymer mass;
c) kneading the polymer mass to form an extensible composition;
d) placing the extensible composition into a mold of the desired geometry having small spaced vent holes for solvent removal;
e) treating the extensible composition in the mold in a vacuum oven at a temperature and time sufficient to cure the composition.

The preparation of precipitated polymers is well-known to the art. In general, the process comprises mixing a dried polymer mix with a solvent, preferably acetone, precipitating the polymer mass from solution with a non-solvent, e.g. ethanol, methanol, ether or water, extracting solvent and precipitating agent from the mass until it is a coherent mass which can be rolled or pressed into a mold, or extruded into a mold, and curing the composition to the desired shape and stiffness. In order to produce an implant having optimal uniform porosity and the desired elasticity coupled with the ability to maintain structural integrity when hand-shaped, kneading of the polymer mass prior to molding is necessary. The kneading may be done by hand or machine and should be continued until the mass becomes extensible, e.g. can be pulled like taffy. Prior to reaching this stage, the polymer mass will snap apart or break when pulled. Curing the polymer in a mold to form an implant having an aspect ratio of three or greater is also important in achieving the desired elasticity.

The temperature and time of molding may be selected, depending on the polymer being used, to achieve the desired elasticity and other properties, as more fully described below.

The mold used for curing the polymer should be perforated with spaced holes or vents, preferably evenly spaced, and preferably having a diameter small enough that the polymeric material does not flow out of the holes, e.g., between about 0.3 mm and about 0.7 mm, and preferably spaced evenly and about 3 mm to about 20 mm apart. This allows solvent and air to escape from the material uniformly as it is cured, so that uniform porosity is achieved. The amount of material used can be varied to vary the percent porosity and pore size of the material, as will be apparent to those skilled in the art.

The molded implant material made by the above method, which may be large blocks having dimensions up to about 30 cm×30 cm×10 cm may be reduced to particles such as by grinding, pulverizing, milling, crushing or shredding, e.g., in a knife mill, to particles having an average diameter between about 50 μm and about 1 cm, preferably between about 250 μm and about 2000 μm. Size fractions having an average particle diameter between about 250 μm and about 850 μm are preferred for dental uses. Size fractions between about 850 μm and about 2000 μm are preferred for other orthopaedic use.

Such particulate material may be mixed with a patient's marrow and blood cells (or other cells) and/or cancellous or other bone graft material to provide an autologous bone graft augmentation or substitute material which can be packed into a wound to promote healing. When this material is made with the stiffness properties of bone, it provides a microenvironment for ingrowing mesenchymal cells closely approximating bone and therefore providing a conducive environment for proliferation of bone progenitor cells and differentiation of bone and marrow. Osteoconductive proteins known to the art may also be included in the material. (See, e.g., Brekke, J. H. (1996), "A Rationale for Delivery of Osteoconductive Proteins," Tissue Engineering 2:97–114.)

A method for implanting the material of this invention is also provided for allowing selected tissue ingrowth into a defect in a patient's body comprising:

a) selecting a biodegradable polymeric implant having an aspect ratio of at least about 3, composed of a material having a Poisson's ratio less than about 0.3;

b) hand-shaping said material to fit said defect;

c) prior to, or after, hand-shaping said material, placing said material into said defect.

Preferably, the implant selected has a stiffness substantially similar to that of the selected tissue.

It is preferred that prior to placing the implant into the defect, it be wetted by soaking, preferably under vacuum, with a biocompatible liquid such as sterile saline, plasma or blood, bone marrow, or other cell suspensions.

The hand-shaped implant may be sutured into place if desired, and/or may be exposed to cross-linking activators whereby its elasticity (tendency to return to its original shape) is decreased, or it may simply be held in place by surrounding soft tissues.

A method is also provided for resurfacing a femoral condyle comprising:

a) hand-shaping into place over at least a portion of the surface of said femoral condyle a sheet of a biodegradable, porous polymeric implant material having a Young's modulus between about 0.1 and about 200 MPa, a Poisson's ratio less than about 0.3, a porosity between about 60 volume percent and about 90 volume percent, wherein the pore size distribution throughout the material is substantially uniform, and having an average pore size of between about 5 μm and about 400 μm, and having an aspect ratio of at least about 3;

b) securing said material to existing cartilage on said femoral condyle;

c) allowing cartilage tissue to ingrow into the pores of said material and subsequently allowing said material to biodegrade, whereby the surface of said femoral condyle is covered with a uniform layer of cartilage.

The uniformity of the layer of cartilage is critical, as lumps and bumps tend to abrade the opposing tissue when the joint is in use, causing damage and pain.

The biodegradable implant materials of this invention can also be used for repair of tissues other than cartilage and bone, including tendons, ligaments and organs such as liver, pancreas, and other organs.

DETAILED DESCRIPTION OF THE PREFERRED EMBODIMENTS

The preferred biodegradable implant materials of this invention are designed to have mechanical properties (e.g. elasticity (Young's modulus) and compressibility (Poisson's ratio) similar to the tissues into which they are designed to be placed. Preferred tissues for placement of the implants of this invention are cancellous bone and articular cartilage. Cartilage phase implant materials with mechanical properties similar to cartilage are also considered to be suitable for use with bone, especially when highly curved regions are to be treated. Cartilage phase implants have a Young's modulus of less than or equal to 1.0 MPa, and bone phase implants have a Young's modulus of greater than or equal to 1.0 MPa. The materials of this invention have a Poisson's ratio less than about 0.3 and preferably less than about 0.1.

The materials are somewhat flexible at room temperature (20° to 25° C.). The cartilage phase material is hand-shapable at normal body temperature e.g. when warmed in the hands or placed into a body cavity, and is more preferably heated to about 45°–50° C. for shaping. The bone phase may be manufactured at varying stiffnesses. The smaller the Young's modulus, the more readily hand-shapable the material will be. Using the methods of this invention, one skilled in the art can shape the implant to fit the tissue defect into which it is to be placed.

Polymers known to the art for producing biodegradable implant materials may be used in this invention. Examples of such polymers are polyglycolide (PGA), copolymers of glycolide such as glycolide/L-lactide copolymers (PGA/PLLA), glycolide/trimethylene carbonate copolymers (PGA/TMC); polylactides (PLA), stereocopolymers of PLA such as poly-L-lactide (PLLA), Poly-DL-lactide (PDLLA), L-lactide/DL-lactide copolymers; copolymers of PLA such as lactide/tetramethylglycolide copolymers, lactide/trimethylene carbonate copolymers, lactide/δ-valerolactone copolymers, lactide ε-caprolactone copolymers, polydepsipeptides, PLA/polyethylene oxide copolymers, unsymmetrically 3,6-substituted poly-1,4-dioxane-2,5-diones; poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolatone, poly-ε-caprolactone, methylmethacrylate-N- vinyl pyrrolidone copolymers, polyesteramides, polyesters of oxalic acid, polydihydropyrans, polyalkyl-2-cyanoacrylates, polyurethanes (PU), polyvinyl alcohol (PVA), polypeptides, poly-β-maleic acid (PMLA), and poly-β-alkanoic acids.

Young's modulus E, a measure of elasticity also referred to as "elastic modulus" is the ratio of stress to strain:

$$E = \frac{\sigma}{\epsilon}$$

where stress σ is the normal force per unit area, and strain ε is the elongation per unit length.

Young's modulus may be measured for the relatively rigid materials of this invention by means known to the art such as the three-point bending test. In this test, a specimen in the form of a wafer is placed horizontally over two "sawhorse"-shaped wedges at both ends. Another wedge, pointed edge down and parallel to the support wedges, is pressed down onto the top of the center of the wafer. Force or load P applied against the top wedge and deflection distance δ are determined. The Young's modulus is calculated:

$$E = \frac{PL^3}{48\delta I}$$

where P is the applied load, L is the distance between end supports, δ is the deflection distance produced by the load P and I is the moment of inertia with respect to the centroidal axis computed from the geometry of the wafer as:

$$I = \frac{bh^3}{12}$$

where b is the width of the wafer and h is the thickness.

Poisson's ratio v may be determined by an indentation test such as that described in allowed U.S. patent application Ser. No. 08/231,612 incorporated herein by reference. In an indentation test, a rigid, cylindrical indenter is pressed into the surface of a specimen such as a wafer of the implant material of this invention. The force P with which the cylinder is pressed into the specimen and the vertical distance the material is indented δ are measured. If the Young's modulus E of the material is known, and if the distance the material is indented δ is very small compared to the height of the material, and the radius r of the cylindrical indenter is very small compared to the height of the material, then Poisson's ratio v can be calculated as:

$$v = \sqrt{1 - \frac{2Er\sigma}{P}}\ .$$

When the Poisson's ratio v is small, i.e. less than about 0.3, such that the material has little tendency to expand sideways, the Young's modulus E (elasticity) is almost the same as the aggregrate modulus $H_A$ of the material.

An important aspect of achieving the desired elastic properties and uniform porosity is kneading the polymer mass during preparation until it becomes extensible. A further important expedient is providing small spaced vent holes in the mold and subjecting the polymer to vacuum extraction of solvent prior to curing, all as described in the Examples hereof.

The temperature at which the polymer is cured is also important in determining the elasticity. For achieving the elasticity of cartilage using a 75:25 PLA/PGA polymer having a molecular weight of approximately 70 kD, a temperature of about 50°–60° C. over a curing time of about 24–48 hours may be used. To achieve the elasticity of bone, a temperature of about 37°–42° C. may be used over a curing time of about 24 hours, followed by a temperature of about 47° C. another 6–24 hours. The mechanical properties of bone, cartilage and other tissues are known to the art, e.g. as described in U.S. patent application Ser. No. 08/196,970 incorporated herein by reference, or may be readily determined by the testing methods described above, or other testing methods known to the art. As some polymers tend to be less elastic than others, the ratio of monomers in the polymer may be adjusted, as will be evident to those of ordinary skill in the art, to achieve the desired properties in the final product. Similarly, the time and temperature of curing may be varied without undue experimentation by those of ordinary skill in the art to achieve the desired properties using the testing methods described above to optimize the process. In addition, cross-linking agents and enhancers, and plasticizers, as known to the art, may be used to modify the desired properties.

The target porosity of the materials of this invention is achieved by adding more or less polymer to the mold. For example, in preparing N number of wafers to have a selected target porosity Q, in a mold having a length a (mm), a width b (mm) and a depth c (mm), using a polymer of density p (g/cm$^{3)}$, the mass of polymer M to be used is calculated by:

$$M = \frac{a \cdot b \cdot c}{1000}\ p(1 - Q)N.$$

As is known to the art, the lifetime of the material in vivo may be increased by increasing the amount of L-PLA content, molecular weight and degree of crystallinity, or decreased by decreasing the same factors. The lifetime of the material may be varied independently of the stiffness as will be apparent to those skilled in the art, for example by increasing the PLA content and at the same time decreasing molecular weight to achieve a longer lifetime without increasing stiffness.

The implant material may incorporate cells, bioactive agents as is known to the art, pH-adjusting agents, for example as described in U.S. patent application Ser. No. 08/361,332 incorporated herein by reference, including Bioglass®, of U.S. Biomaterials, which is also useful for binding growth factors, and other additives known to the art such as matrix vesicles or matrix vesicle extracts as described in U.S. patent application Ser. No. 08/250,695, incorporated herein by reference, and other bioceramics.

Wafers formed of the materials of this invention may be readily die-punched to uniformly produce implants of various sizes and shapes. Multi-phase wafers prepared as described in the Examples hereof may also be punched to produce multi-phase implants of different sizes and shapes, preferably to produce cylindrical two-phase implants.

A preferred honeycomb lattice material of this invention is prepared by die-punching holes of a diameter of about 1 mm to about 4 mm, preferably about 2 mm, in a wafer having a thickness of about 1 mm to about 4 mm, preferably about 3 mm. The holes are spaced approximately 2 mm to about 4 mm apart. The wafer after punching out the holes is referred to herein as a "honeycomb lattice" material. This honeycomb lattice material is more flexible than the unpunched wafer and is preferred, using bone-phase material, for bone repair such as bone graft onlay for various bone repairs including spinal fusion, that require shaping of the implant. In this process, the honeycomb lattice material is allowed to soak in a mixture of blood and marrow cells prior to affixing into the bone defect.

The small cylindrical chunklets punched out of the honeycomb lattice material preferably have a volume between about 1 $mm^3$ and about 16 mm3 per chunklet. They are useful as a sterile substitute for allogenic and autologous bone filler materials in bone graft procedures. These chunklets may be packed into the defect and used as bone graft filler when other types of bone graft material are at a minimum. It is preferred that bone-phase chunklets be used for this purpose. These chunklets, having mechanical properties (e.g. elasticity) and physical properties (e.g. porosity) similar to those of bone, provide the ingrowing cells with an environment as close as possible to their natural environment, thus fostering and encouraging growth of the cells.

The polymeric implant materials of this invention may be shaped to any desired geometry up to cubic volumes of about 900° C. Shredded or carved pieces of the implant material are especially useful as substitutes or extenders for bone graft material.

EXAMPLES

Example 1

Method of Making Polymeric Wafers, Cylindrical Implants, Honeycomb Lattices and Chunklets.

Five grams of PLA/PGA (75:25) polymer, molecular weight 80,000 D, intrinsic viscosity about 0.6 to about 0.75 in chloroform, were weighed into a Teflon beaker. A ¾" Teflon-coated magnetic stirring bar was placed in the beaker and the beaker placed on a magnetic stirplate. 30 ml acetone was added and the mixture stirred (at setting 8 on the stirplate) for about 20 minutes until the polymer was completely dissolved. Polymer was precipitated by adding 30 ml ethanol and stirring for about 20 seconds (at setting 3 on the stirplate) to agglomerate the polymer gel mass.

The supernatant liquid was then decanted and the gel mass turned onto a Teflon plate to be used as a work surface. The stirbar was separated from the mass by using a Teflon policeman, recovering as much polymer as possible. Excess liquid was blotted away using care not to touch the polymer with the Kimwipe blotter. The polymer mass was then rolled and flattened to a thin sheet (1±0.1 mm thick) using a bar of round Teflon stock about ¾" in diameter.

The Teflon plate with the polymer was then placed in a vacuum desiccator, and vacuum was applied for several minutes (2 to 4.5 min) using a KNF reciprocating diaphragm vacuum pump until the polymer mass became blistered and bubbly as the solvent was removed. The vacuum was released and the Teflon plate with the polymer was removed from the desiccator. Using rubber gloves, the polymer gel was hand-rolled into a ball and kneaded using thumbs and forefingers until the material became soft and extensible. During this process a small amount of residual solvent was released and the polymer felt slightly wet. Kneading was continued until no more liquid was evident. The gel was then rolled out into a thin sheet using the Teflon bar and being careful not to allow the polymer to wrap around the bar, as the polymer at this point was quite sticky and readily adhered to itself upon contact.

The polymer was then again placed in the desiccator and vacuum was applied for several more (2 to 4.5) minutes until the gel expanded and appeared "foamy," having many fine bubbles distributed throughout the matrix. The polymer was removed from vacuum and again kneaded as before until it was soft and extensible and took on the lustre of spun sugar and a "satiny" appearance. The mass of the polymer gel at this point was recorded.

The polymer gel was then divided into five equal pieces, and the pieces were shaped to fit the well of a mold. The mold was wafer-shaped, approximately 20 mm×40 mm×3 mm, and perforated with holes having a 0.7 mm diameter spaced approximately 3 mm to 10 mm apart. Care was taken to shape each piece to fit the well of the mold, making sure that the surface was uniform and even with no thin spots and that the material filled the mold edge to edge. The molds (without top) were then placed into the desiccator and vacuum was applied for two minutes. The molds were then removed from the desiccator and the tops of the wafers flattened without completely compressing the expanded polymer. The top plates of the molds were then affixed using appropriate nuts and bolts.

The molds were then placed in a vacuum oven at 60°–65° C. under vacuum of less than 50 mTorr for 24–48 hours. For cartilage phase materials, i.e. wafers having mechanical properties of cartilage, the treatment vacuum oven was continued at the same temperature for an additional 24 hours. After curing, the polymer was substantially free of solvent.

The resulting polymeric cartilage phase wafers were uniform in porosity, having an average pore size of about 100 $\mu$m and a percent porosity of about 65 volume percent. They were flexible and, when slightly warmed in the hand to about body temperature, were easily hand-shapable.

The resulting polymeric bone phase wafers were also uniform in porosity, having an average pore size of about 150 $\mu$m and a percent porosity of about 70 volume percent. Although they were not as flexible as the cartilage phase wafers at room temperature, they could be hand-shaped at body temperature.

A polymeric gel mass as described above was placed into a spherical mold perforated as described above, approximately 1 inch in diameter, and treated in the vacuum oven for 24 hours at 42° C., then at 47° C. for about 24 hours. The resultant polymeric sphere had a porosity of 70 volume percent and an average pore size of about 150 $\mu$m. Smaller and larger spheres can be molded using this technique.

Two-phase cylindrical implants having a cartilage phase atop a bone phase as described in PCT Publication WO 9315694 were made by layering the prepared cartilage phase over a preformed bone phase. The bone phase was prepared as described above, then polymer gel to form the cartilage phase was overlaid on the bone phase and the two-phase wafer was vacuum treated for 48 hours at 50 mTorr at 42° C. Two-phase cylindrical implants were then die-punched using the appropriate size cutter, e.g. for osteochondral defects, a 1.0 mm thick cartilage phase was layered over a 2 mm thick bone phase, and a 2–7 mm diameter cylinder was cut from the resulting two-phase wafer.

Uniform cylindrical chunklets suitable for use in filling bone defects as an alternative bone graft material were punched out of bone-phase wafers formed by the process described above, having a thickness of about 2 mm, with a 2 mm punch, leaving evenly spaced holes in the wafer approximately 3 mm apart.

The wafers from which the implants and chunklets were removed had a honeycomb lattice structure and were suitable for use as implants for promoting healing of bone defects, including spinal fusions.

Example 2

Use of Hand-Shapable Cartilage Phase Material for Femoral Condyle Resurfacing.

A portion of the cartilage covering the femoral condyle surface of a patient, in which a defect has been noted, is removed to form a regular-shaped recess. A cartilage phase wafer of Example 1 having a thickness the same as that of the recess to be filled is cut to form an implant sized to fit the recess then pressed and hand-shaped into the recess so as to exactly fit with no portion raised above the cartilage surface. The implant is then sutured into place with 9.0 Vicryl sutures, and the site closed. The implant material maintains its structural integrity for a period of 4–10 weeks while new tissue grows into the defect. The new cartilage forms a smooth, uniform surface over the femoral condyle within a period of about six weeks, and the implant degrades and disappears within a period of about 8–16 weeks.

Example 3

Use of Honeycomb Lattice Material for Bone Graft Onlay.

Bone phase honeycomb lattice material as described in Example 1 is used to foster bone regrowth. This implant can be used to strengthen, via onlay, weakened bone, or it can be used to shape and conform to spinal pedicles for spinal fusion. The honeycomb lattice material is saturated with blood and marrow by soaking and may be sutured into place using standard suturing techniques. Over the course of approximately two to six weeks, new bone grows into the implant to strengthen or fuse a defect area, and the implant subsequently degrades and disappears.

Example 4

Preparation of Bone Graft Substitute/Extender Material in Chunklet and Shredded Form The implants used for this study were made from a 75:25 DL PLA/PGA copolymer with intrinsic viscosity (I.V.)=0.83 (Birmingham Polymers Inc. Lot # 101-100-1) in a clean room environment without terminal sterilization. The I.V. was determined in HFIP at 30° C.

Two different geometries of the materials were prepared. Cylindrical bone graft extenders were made by punching cylinders (1.5 mm diameter×1.5 mm high) from wafers (60×60×1.5 mm) made by the method of Example 1. Shredded extenders were made by shredding wafers in a Leibinger Tessier osseous microtome (Leibinger & Fischer LP, Irving, Tex.). The shredded particles were then placed into a sieve and shaken. The fraction between 10 and 20 mesh (850–2000 μm) was collected for use in these studies. The shredded fragments were of approximately the same dimensions as the chunklets and were irregularly shaped. All materials were packaged in sterile Eppenderoff tubes and placed in sterile autoclave bags.

Example 5

Use of Bone Graft Substitute Material as Bone Graft Extenders.

The shredded material and chunklets of Example 4 were used to study wound healing in 30 6-month old male adult New Zealand White (NZW) rabbits.

Ostectomies 1 cm in length were created in the diaphysis of the right ulna of each rabbit: 6 rabbits received autologous cancellous bone chips (CAN); 6 rabbits received CAN and 20 chunklet particles (50:50 v/v); 6 rabbits received 40 chunklet particles; 6 rabbits received an equivalent weight of shredded particles; and 6 rabbits were untreated (EMP). Periosteum overlying the defect site was retained whenever possible and no internal fixation was used. The defects were examined radiographically at 6 and 12 weeks and histologically at 12 weeks. At 6 weeks there was radiographic evidence of healing in all groups at the ostectomy lines; healing in the treatment groups was enhanced with no obvious differences as a function of implant type. At 12 weeks, the untreated controls were mechanically unstable to manual palpation. In contrast, the majority of the treatment specimens were mechanically stable. Radiographically, there were no significant qualitative differences among the treatment groups; all were better than the untreated control. Statistical analysis of semi-quantitative measures showed significant differences between the chunklet containing groups and the EMP group. In general, histological results supported the radiographic evaluations. When autologous bone graft (100 or 50%) was used, cortical plates were restored. While this was delayed in the 100% chunklet and shredded particle animals, bony union was generally complete and only small amounts of residual scaffold remained. In contrast, the entire width and length of the defect was not bridged in any of the EMP specimens. There was mild to moderate focal inflammation in all treatment groups associated with the implants. The inflammation did not appear to impair the wound healing response, and repair mechanisms in the treatment were normal. At 12 weeks, healing was not complete in any of the animals; however, the post-mortem gross observations, radiographic, and histological evaluations indicate that normal healing is occurring in the chunklet and shredded material treatment groups and that these materials may be effectively utilized as a bone graft extenders or bone graft substitutes.

We claim:

1. A composition suitable for band-shaping for use as a tissue implant comprising a molded biodegradable, porous polymeric implant material having a Poisson's ratio at room temperature less than about 0.3, a porosity between about 60 volume percent and about 90 volume percent, wherein the pore size distribution throughout the material is substantially uniform, said implant material being molded into a shape having an aspect ratio of about 3 or more, wherein said molded implant material is hand-shapable at body temperature without loss of structural integrity.

2. The composition of claim 1 wherein said implant material is made of a copolymer of PLA and PGA.

3. The composition of claim 1 wherein said implant material is shaped to fit a bone or cartilage defect.

4. The composition of claim 1 wherein said implant material has a Young's modulus between about 0.1 and about 200 MPa at room temperature.

5. The composition of claim 1 wherein said implant material has a Young's modulus between about 0.1 and about 10 MPa at room temperature.

6. The composition of claim 1 wherein said implant material has a Young's modulus between about 0.1 and about 10 MPa at shaping temperature.

7. The composition of claim 1 wherein said implant material has a porosity of between about 60 volume percent and about 80 volume percent.

8. The composition of claim 1 wherein said implant material is fabricated in sheets having a thickness between about 4 mm and about 100 mm.

9. The composition of claim 8 wherein said sheets are perforated with spaced holes having a diameter between about 1 mm and about 4 mm and spaced about 2 mm to about 4 mm apart.

10. The composition of claim 1 wherein said implant material is shaped to repair a fractured orbital bone.

11. The composition of claim 1 wherein said implant material is shaped to correct a chin defect.

12. The composition of claim 1 wherein said implant material is shaped to correct an alveolar ridge defect.

13. The composition of claim 1 wherein said implant material comprises bioactive agents and is capable of releasing said bioactive agents in use over time.

14. The composition of claim 1 wherein said implant material comprises Bioglass.

15. The composition of claim 1 wherein said implant material is substantially free of residual solvent.

16. The composition of claim 1 wherein said implant material is capable of maintaining structural integrity in vivo for at least about two weeks.

17. A composition suitable for making a tissue implant comprising a molded, porous, biodegradable implant material having a porosity between about 60 and 90 volume percent wherein the pore size distribution throughout the material is substantially uniform, and wherein said implant material is formed into a shape having at least one dimension greater than about 7 mm by molding in a mold perforated with spaced perforations to allow substantially uniform escape of gas during molding.

18. The composition of claim 17 wherein said implant material has a porosity between about 60 and about 80 volume percent.

19. The composition of claim 17 wherein said implant material is hand-shapable at body temperature without loss of structural integrity.

20. The composition of claim 17 wherein said implant material has a Young's modulus at room temperature of about 0.1 to about 200 MPa.

21. The composition of claim 17 wherein said implant material has a Young's modules at room temperature of about 1.0 to about 1700 MPa.

22. A method of implanting a biodegradable polymeric material having uniform pores for selected tissue ingrowth into a defect in a patient's body comprising:

a) selecting a biodegradable polymeric implant composed of a material having a Poisson's ratio less than about 0.3;

b) hand-shaping said material to fit said defect; and c) placing said material into said defect prior to, or after, hand-shaping said material.

23. The method of claim 22 wherein said material of step b) is sutured into place.

* * * * *

UNITED STATES PATENT AND TRADEMARK OFFICE

CERTIFICATE OF CORRECTION

PATENT NO. : 5,863,297

DATED : January 26, 1999

INVENTOR(S) : Walter et al.

It is certified that error appears in the above-identified patent and that said Letters Patent is hereby corrected as shown below:

In column 14, line 31, claim 1, delete "band-shaping" and replace with --hand-shaping--.

In column 14, line 59, claim 8, delete "4 mm" and replace with -- .4 mm--.

Signed and Sealed this

Thirteenth Day of July, 1999

*Attest:*

Q. TODD DICKINSON

*Attesting Officer*

*Acting Commissioner of Patents and Trademarks*